United States Patent
Cho et al.

(10) Patent No.: US 10,183,048 B2
(45) Date of Patent: Jan. 22, 2019

(54) COMPOSITION FOR PROMOTING THE ACTIVITY OF PEROXISOME PROLIFERATOR-ACTIVATED RECEPTOR-DELTA

(75) Inventors: Si Young Cho, Seoul (KR); Pil Joon Park, Yongin-si (KR); Ji Hae Lee, Yongin-si (KR); Dae Bang Seo, Yongin-si (KR); Sang Jun Lee, Seongnam-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 653 days.

(21) Appl. No.: 13/511,964

(22) PCT Filed: Nov. 25, 2010

(86) PCT No.: PCT/KR2010/008404
§ 371 (c)(1),
(2), (4) Date: May 24, 2012

(87) PCT Pub. No.: WO2011/065767
PCT Pub. Date: Jun. 3, 2011

(65) Prior Publication Data
US 2013/0045289 A1 Feb. 21, 2013

(30) Foreign Application Priority Data

Nov. 26, 2009 (KR) .......................... 10-2009-0115024

(51) Int. Cl.
*A61K 36/282* (2006.01)
*A23L 33/105* (2016.01)

(52) U.S. Cl.
CPC .......... *A61K 36/282* (2013.01); *A23L 33/105* (2016.08); *A23V 2002/00* (2013.01)

(58) Field of Classification Search
None
See application file for complete search history.

(56) References Cited

U.S. PATENT DOCUMENTS 8,741,364 B2 * 6/2014 Ninomiya ............ A61K 31/205
424/725

FOREIGN PATENT DOCUMENTS

| CN | 1544018 A | | 11/2004 |
|---|---|---|---|
| JP | 2006016312 A | * | 1/2006 |
| KR | 1993-0008763 B1 | | 9/1993 |
| KR | 2001110003 A | * | 12/2001 |
| KR | 2004065427 A | * | 7/2004 |
| KR | 10-2005-0121775 A | | 12/2005 |
| KR | 10-0645385 B1 | | 11/2006 |
| KR | 10-0659138 B1 | | 12/2006 |
| KR | 10-2007-0042405 A | | 4/2007 |
| KR | 10-2007-0091964 A | | 9/2007 |
| KR | 10-2008-0050348 A | | 6/2008 |
| KR | 10-2008-0054682 A | | 6/2008 |
| KR | 10-2008-0065234 A | | 7/2008 |

OTHER PUBLICATIONS

Wang et al., Bioactives of *Artemisia dracunculus* L enhance cellular insulin signaling in primary human skeletal muscle culture, 2008, Metabolism Clinical and Experimental, 57:S58-S64.*
2016 https://examine.com/supplements/artemisia-iwayomogi/#ref8.*
U.J. Jung et al., "The Anti-Diabetic Effects of Ethanol Extract from Two Variants of Artemisia Princeps Pampanini in C57BL/KsJ-db/db Mice," Food and Chemical Toxicology, vol. 45, pp. 2022-2029, 2007.
S. Lim et al., "Effect of *Artemisia princeps* Var *orientalis* and *Circium japonicum* Var *ussuriense* on Serum Lipid of Hyperlipidemic Rat," The Korean Nutrition Society, vol. 30(1), pp. 12-18, 1997.
V. A. Narkar et al., "AMPK and PPARδ Agonists are Exercise Mimetics," Cell, vol. 134, pp. 1-11, Aug. 8, 2008.
Y. Wang et al., "Peroxisome-Proliferator-Activated Receptor δ Activates Fat Metabolism to Prevent Obesity," Cell, vol. 113, pp. 159-170, Apr. 18, 2003.
G.D. Barish, et al., "PPARδ: A Dagger in the Heart of the Metabolic Syndrome," The Journal of Clinical Investigation, vol. 116, No. 3, pp. 590-597, Mar. 2006.

* cited by examiner

*Primary Examiner* — Terry A McKelvey
*Assistant Examiner* — Catheryne Chen
(74) *Attorney, Agent, or Firm* — Blank Rome LLP

(57) ABSTRACT

Disclosed is a composition for promoting the activity of peroxisome proliferator-activated receptor-δ (PPAR-δ), which contains *Artemisia vulgaris* extracts or *Artemisia capillaris* extracts as active ingredients. The composition is effective in strengthening muscles, improving endurance and memory, and preventing and alleviating the symptoms of dementia or Parkinson's disease.

3 Claims, 4 Drawing Sheets

COMPOSITION FOR PROMOTING THE ACTIVITY OF PEROXISOME PROLIFERATOR-ACTIVATED RECEPTOR-DELTA

TECHNICAL FIELD

The present disclosure relates to a composition including *Artemisia* extract as an active ingredient.

BACKGROUND ART

Peroxisome proliferator-activated receptors (PPARs) are ligand-activated transcription factors belonging to the nuclear receptor superfamily activated by fatty acids. The PPAR family consists of PPAR-α, PPAR-β/δ and PPAR-γ, which show different ligand specificity and tissue distribution. PPAR-α is expressed the most in the liver and promotes fatty acid oxidation in peroxisomes and mitochondria. PPAR-γ is expressed in adipose tissues and regulates storage of fats. The ligand of PPAR-α, fibrate, is used as hypolipidemic agent, and the ligand of PPAR-γ, thiazolidinedione, is used in the treatment of diabetes mellitus type 2.

PPAR-δ is expressed in muscles, brown adipose tissues, etc. This transcription factor shows anti-obesity effect since fatty acid oxidation in adipocytes is promoted in mice in which it is overexpressed (Wang Y X et al., *Cell,* 113, pp. 159-170, 2003). An activator of PPAR-δ promotes metabolism in skeleton muscle cells, improves insulin sensitivity, reduces adipocytes and inhibits inflammatory response by increasing expression of such proteins as carnitine palmitoyltransferase 1β (CPT1β) and pyruvate dehydrogenase kinase isozyme 4 (PDK4) (Barish G D et al., *J. Clin. Invest.,* 116, pp. 590-597, 2006, 116:590). When the ligand of PPAR-δ, GW501516, was administered together with the AMP-activated protein kinase (AMPK) activator AICAR to a mouse, the mouse showed strengthened muscles even without exercise as well as anti-obesity effect (Vihang A N et al., *Cell,* 134, pp. 1-11, 2008).

However, activator or ligand of PPAR-δ with proven stability has not been found yet. The inventors of the present disclosure have found out that *Artemisia iwayomogi* extract contains a novel ligand capable of activating PPAR-δ.

DISCLOSURE

Technical Problem

An embodiment of the present disclosure is directed to providing a composition including *Artemisia* extract.

Another embodiment of the present disclosure is directed to providing food, health-food supplement and pharmaceutical compositions that include the composition including *Artemisia* extract.

Technical Solution

In one general aspect, the present disclosure provides a composition including *Artemisia princeps* or *Artemisia iwayomogi* extract as an active ingredient.

Advantageous Effects

The composition according to the present disclosure has the effect of promoting the activity of PPAR-δ and is effective in promoting muscular metabolism and improving memory. The composition may be variously used in the field of food, health-food supplements or pharmaceuticals.

BEST MODE

Figure 1:
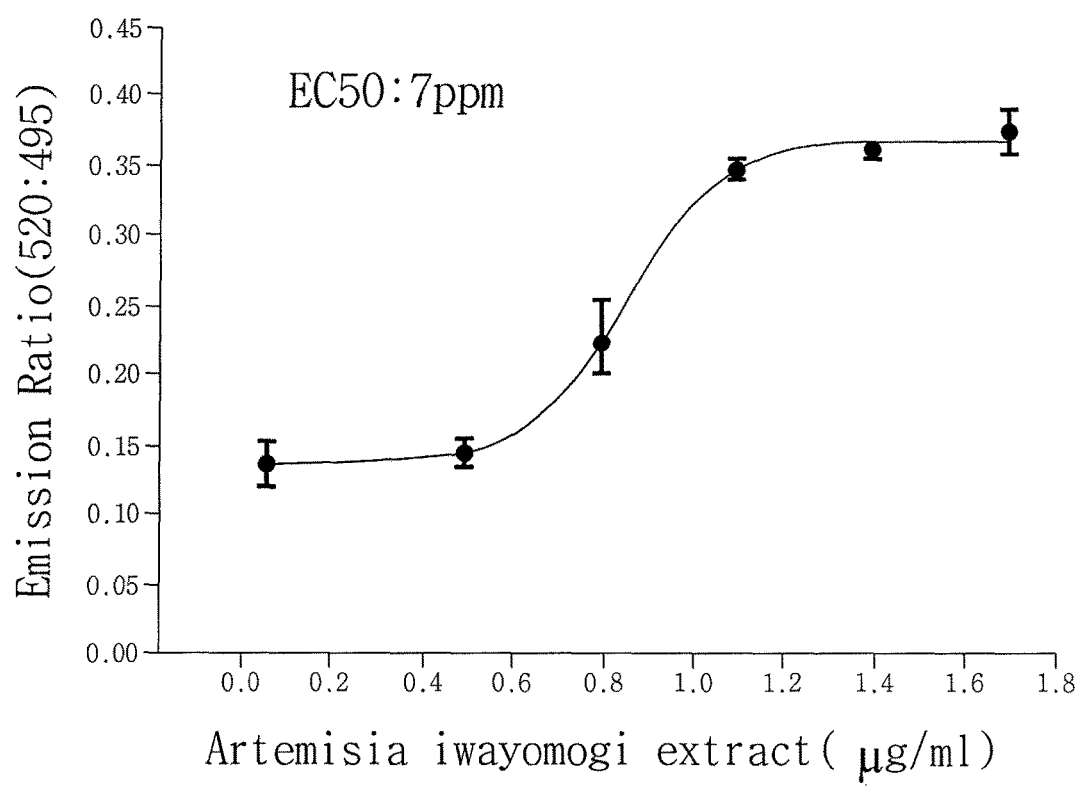
FIG. 1 shows fluorescence data showing PPAR-δ-LBD binding affinity of *Artemisia iwayomogi* extract in a test tube.

A composition according to an exemplary embodiment of the present disclosure comprises *Artemisia* extract as an active ingredient. The composition comprising. *Artemisia* extract promotes the activity of peroxisome proliferator-activated receptor delta (PPAR-δ) and is effective in promoting muscular metabolism and/or improving memory.

In the present disclosure, *Artemisia* (ssuk, *Artemisia princeps*) collectively refers to dicotyledonous perennial grasses belonging to the family Asteraceae of the order Asterales. *Artemisia* grows naturally in the whole area of Korea and has been widely used for food as vegetable, soup, porridge, cake, etc.

In an exemplary embodiment, the *Artemisia* extract may be *Artemisia iwayomogi* extract. *Artemisia iwayomogi* is a perennial grass belonging to the genus *Artemisia* of family Asteraceae. It is also called saengdang ssuk, aedang ssuk, sacheol ssuk, injincho, heat reliever, heuinsan ssuk or teolsan ssuk. In particular, the young leaves are called injin or heat reliever and traditionally have been used as food or folk medicine owing to peculiar fragrance and medicinal effect. Injin, the young bud of sacheol ssuk which is a perennial grass belonging to the family Asteraceae, has been known from old times to be beneficial for the liver. Especially, it is known to be highly effective in jaundice. Injin promotes secretion of bile and clears the liver by excreting lumps, cholic acid and bilirubin in the bile. Also, it reduces blood pressure, relieves fever, and kills various germs including tubercle *bacillus*. In addition, it is effective in degrading lipids, dilating coronary arteries and promoting urination.

In an exemplary embodiment, the composition has the effect of regulating the expression of enzymes that promote fat and sugar metabolism in muscle cells. Specifically, the composition which comprises *Artemisia princeps* or *Artemisia* iwayomogi extract as an active ingredient is effective in promoting the expression of proteins that promote fat and sugar metabolism in muscles, as ligand activating PPAR-δ. In an exemplary embodiment, the composition may be a composition for strengthening muscles and/or improving endurance. In another exemplary embodiment, the composition may be a composition for preventing and/or alleviating the symptoms of dementia or Parkinson's disease. These effects may be achieved through promotion of the PPAR-δ activity.

In an exemplary embodiment, the composition may comprise 1-100 wt %, specifically 1-80 wt % of the *Artemisia princeps* or *Artemisia iwayomogi* extract based on the total weight of the composition. More specifically, the *Artemisia*

*princeps* or *Artemisia iwayomogi* extract may be included in an amount of 10-60 wt % based on the total weight of the composition. The above-described content of the *Artemisia princeps* or *Artemisia iwayomogi* extract is an effective content for activating PPAR-δ.

A process for preparing the *Artemisia princeps* or *Artemisia iwayomogi* extract according to the present disclosure is not particularly limited. The *Artemisia princeps* or *Artemisia iwayomogi* extract may be extracted using water or an organic solvent. The organic solvent may be selected from, for example, a group consisting of ethanol, methanol, butanol, ether, ethyl acetate, chloroform and a mixture of the organic solvent with water. For example, the *Artemisia princeps* or *Artemisia iwayomogi* extract may be obtained by repeating a procedure of adding 70% ethanol (3 L) to *Artemisia princeps* or *Artemisia iwayomogi* (300 g) and stirring at 70-80° C. for 3 hours 2 times. Thus obtained extract may be filtered through Whatman No. 1 filter paper and freeze dried at −70° C. to obtain the *Artemisia princeps* or *Artemisia* iwayomogi extract in solid form.

The composition according to an exemplary embodiment of the present disclosure is applicable not only to animals but also to human. The present disclosure also provides a food or health-food supplement composition comprising the above-described composition. The food or health-food supplement composition may be prepared, for example, into tablet, granule, drink, caramel, diet bar, tea powder, typical tea bag, etc., but are not particularly limited thereto. The compositions may be prepared by those skilled in the art without special difficulty using the active ingredient and other ingredients commonly used in the art considering particular preparation type or purpose of use. A synergic effect may be achieved when the active ingredient is used in combination with other ingredients.

The present disclosure also provides a pharmaceutical composition comprising the above-described composition. The pharmaceutical composition may further comprise a pharmaceutical adjuvant such as preservative, stabilizer, wetting agent or emulsifier, salt for osmotic control and/or buffer or other therapeutically useful substance, and may be formulated into various oral or parenteral administration forms according to methods known in the art.

Formulations for oral administration include, for example, tablet, pill, hard and soft capsule, liquid, suspension, emulsion, syrup, powder, dust, fine granule, granule, pellet, etc. These formulations may comprise a surfactant, a diluent (e.g. lactose, dextrose, sucrose, mannitol, sorbitol, cellulose or glycine) and a lubricant (e.g. silica, talc, stearic acid and its magnesium or calcium salt, or polyethylene glycol) in addition to the active ingredient. Further, the a tablet may comprise a binder (e.g. magnesium aluminum silicate, starch paste, gelatin, tragacanth, methyl cellulose, sodium carboxymethyl cellulose or polyvinylpyrrolidone) and, as occasion demands, it may also comprise a pharmaceutical additive such as a disintegrant, an absorbent, a colorant, a flavor, a sweetener, etc., e.g. starch, agar, alginic acid or its sodium salt. The tablet may be prepared by the common mixing, granulation or coating method. And, formulations for parenteral administration include, for example, injection, medicinal drop, ointment, lotion, gel, cream, spray, suspension, emulsion, suppository or patch, but are not limited thereto.

The pharmaceutical composition according to the present disclosure may be administered orally or parenterally, e.g. rectally, topically, transdermally, intravenously, intramuscularly or subcutaneously.

A pharmaceutically acceptable dosage, i.e. administration dosage, of the active ingredient will vary depending on the age, gender and body weight of the subject, particular disease or pathological condition to be treated, severity of the disease or pathological condition, administration route and discretion of a diagnoser. Determination of the administration dosage considering these factors is in the level of those skilled in the art. A general administration dosage may be 0.01-2000 mg/kg/day, specifically 1-100 mg/kg/day. However, this administration dosage does not limit the scope of the present disclosure by any means.

The composition according to the present disclosure may be prepared into various types of composition for external skin application, more specifically a cosmetic composition. For example, it may be prepared into softening lotion, astringent lotion, nourishing lotion, eye cream, nourishing cream, massage cream, cleansing cream, cleansing foam, cleansing water, powder, essence, pack, etc., but is not particularly limited thereto.

The composition according to the present disclosure which contains *Artemisia princeps* or *Artemisia iwayomogi* extract as an active ingredient has the effect of promoting the activity of PPAR-δ. The effect of a substance promoting the activity of PPAR-δ of strengthening muscles, improving endurance and memory, and preventing or alleviating the symptoms of dementia or Parkinson's disease is known in the art. Experimental details can be found in Korean Patent Application Publication Nos. 10-2008-0050348 and 2008-0065234.

MODE FOR INVENTION

The examples and experiments will now be described. The following examples and experiments are for illustrative purposes only and not intended to limit the scope of this disclosure.

Example 1

Preparation of *Artemisia iwayomogi* Extract

*Artemisia iwayomogi* cultivated in Chengcheon-dong, Jecheon-si, Chungcheongbuk-do, Korea was purchased. After adding 70% ethanol (3 L) to *Artemisia iwayomogi* (300 g), the mixture was stirred at 70-80° C. for 3 hours. This procedure was repeated 2 times and extract was obtained by filtering through filter paper. The filtrate was concentrated under reduced pressure using a rotary vacuum evaporator and then freeze dried to obtain dry powder (29 g).

Test Example 1

PPAR-δ-LBD Binding Affinity of *Artemisia Iwayomogi* Extract

PPAR-δ is activated when a ligand is attached to the ligand binding domain (LBD) of this protein and regulates expression of other genes. Therefore, a substance activating this transcription factor should be able to bind to the LBD. In order to investigate whether *Artemisia iwayomogi* extract can activate PPAR-δ, the following experiment was performed using the *Artemisia iwayomogi* extract prepared in Example 1.

The *Artemisia iwayomogi* extract was dissolved in dimethyl sulfoxide (DMSO) and PPAR-δ-LBD binding affinity was quantified by measuring fluorescence using an assay kit (LanthaScreen TR-FRET peroxisome proliferator receptor delta coactivator assay kit; Invitrogen, CA).

The result is shown in FIG. 1. As seen from FIG. 1, fluorescence intensity increased in a manner dependent on the concentration of the *Artemisia iwayomogi* extract. The $EC_{50}$ value for PPAR-δ-LBD ligand of the *Artemisia iwayomogi* extract was 7 μg/mL.

Test Example 2

PPAR-δ Reporter Activating Effect of *Artemisia iwayomogi*

In order to investigate whether the *Artemisia iwayomogi* extract actually activates PPAR-δ, the following experiment was performed using a human PPAR-δ reporter assay kit (NR1C2, PPAR-δ/β) Reporter Assay kit (Indigo Biosciences, Inc.).

PPAR-δ reporter cells were added to CRM-1 medium (Indigo Biosciences, Inc.), seeded on a 96-well plate, cultured for 4 hours, and then treated with the *Artemisia iwayomogi* extract at concentrations of 50, 100 and 200 μg/mL. 1 μM GW501516 (Alexis Biochemicals, USA) well known as a ligand of PPAR-δ was used as positive control, and DMSO of 1/1000 volume equivalent of the medium was used as negative control. After incubation at 37° C. for 20 hours in a 5% $CO_2$ incubator, the medium was discarded and reaction was performed at room temperature for 10 minutes after adding Luc detection reagent. Then, the activity of luciferase reporter expressed by PPAR-δ was analyzed using a luminometer.

Figure 2:
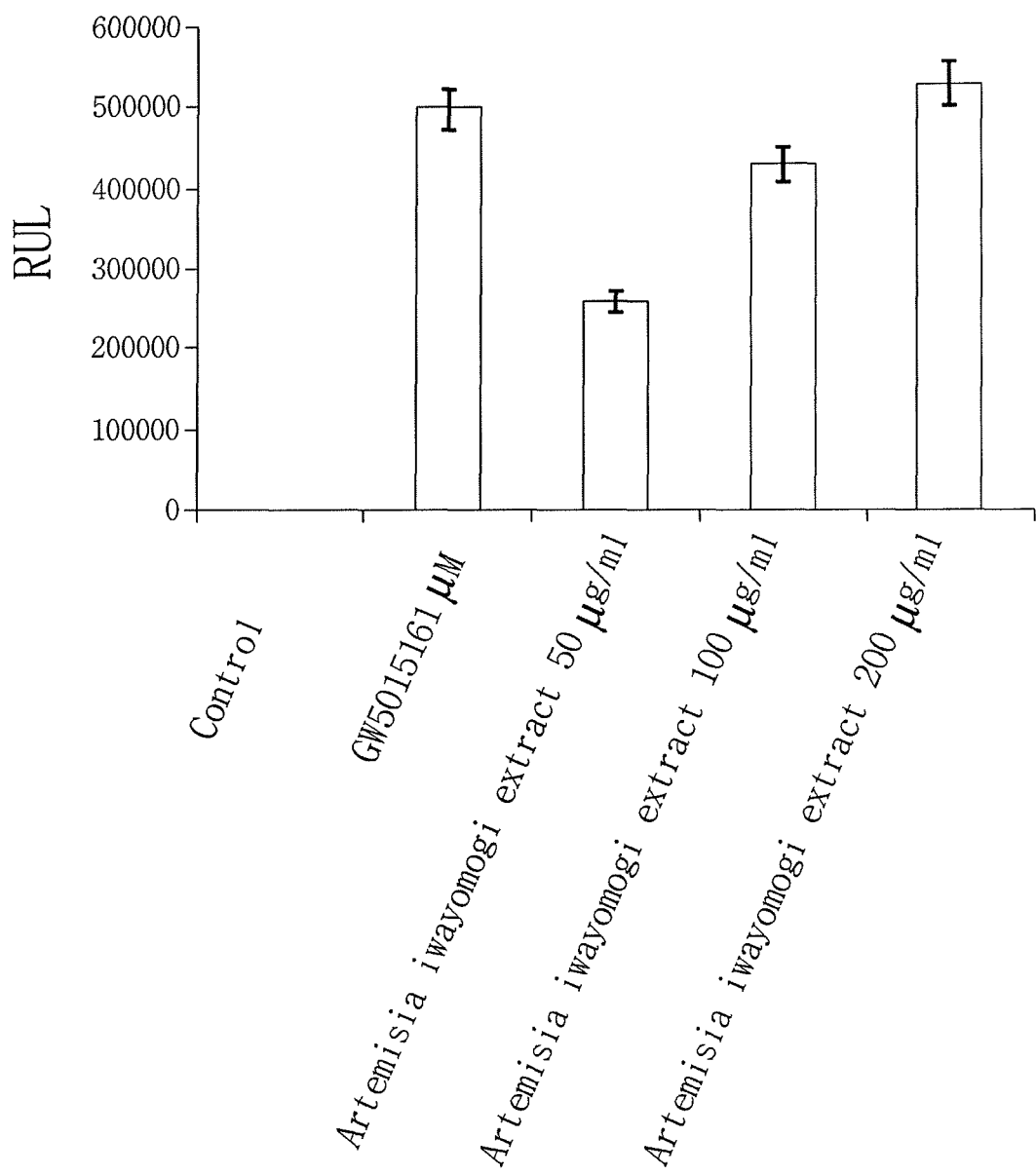
FIG. 2 shows expression level of the reporter gene luciferase as a result of PPAR-δ activation by *Artemisia iwayomogi* extract.

The result is shown in FIG. 2. As seen from FIG. 2, it was confirmed that the *Artemisia iwayomogi* extract expresses the reporter gene more than negative control by activating PPAR-δ.

Test Example 3

Regulation of Expression of Genes Involved in Fatty Acid and Sugar Metabolism in Muscle Cells of *Artemisia iwayomogi* Extract In order to analyze the effect of the *Artemisia iwayomogi* extract on the regulation of expression of genes involved in fatty acid and sugar metabolism in muscle cells, the *Artemisia iwayomogi* extract prepared in Example 1 was dissolved in DMSO and the following experiment was performed.

Immature C2C12 muscle cells were acquired from the American Type Culture Collection (ATCC; USA) and cultured in Dulbecco's modified Eagle's medium (DMEM; Gibco 1210-0038) containing 10% fetal bovine serum (FBS) until 70% confluency in a 5% $CO_2$ incubator while replacing the medium every other day. The cells were induced to differentiate into muscle cells by culturing in a medium containing 2% horse serum (HS). After culturing for 4 days in the medium containing 2% HS, the muscle cells were treated with 200 μg/mL *Artemisia iwayomogi* extract. A control group was treated with DMSO (1/1000 volume equivalent of the medium). The treated cells were cultured at 37° C. for 24 hours and, after washing 2 times with cold saline, RNA was extracted using TRIzol agent (Invitrogen). Then, cDNA was synthesized using the extracted 1 μg/μL RNA, using a reverse transcription PCR system (Promega).

Expression level of genes such as CPT1β, PDK4 and GAPDH was measured using the synthesized cDNA as well as a primer and a probe designed for the genes (Applied Biosystems; CPT1β, Mm00487200_m1, PDK4, Mm00447181 ml, GAPDH, Mm99999915_q1). The PCR reaction and analysis were performed using the Rotor-Gene 3000 system (Corbett Research, Sidney, Australia).

Figure 3:
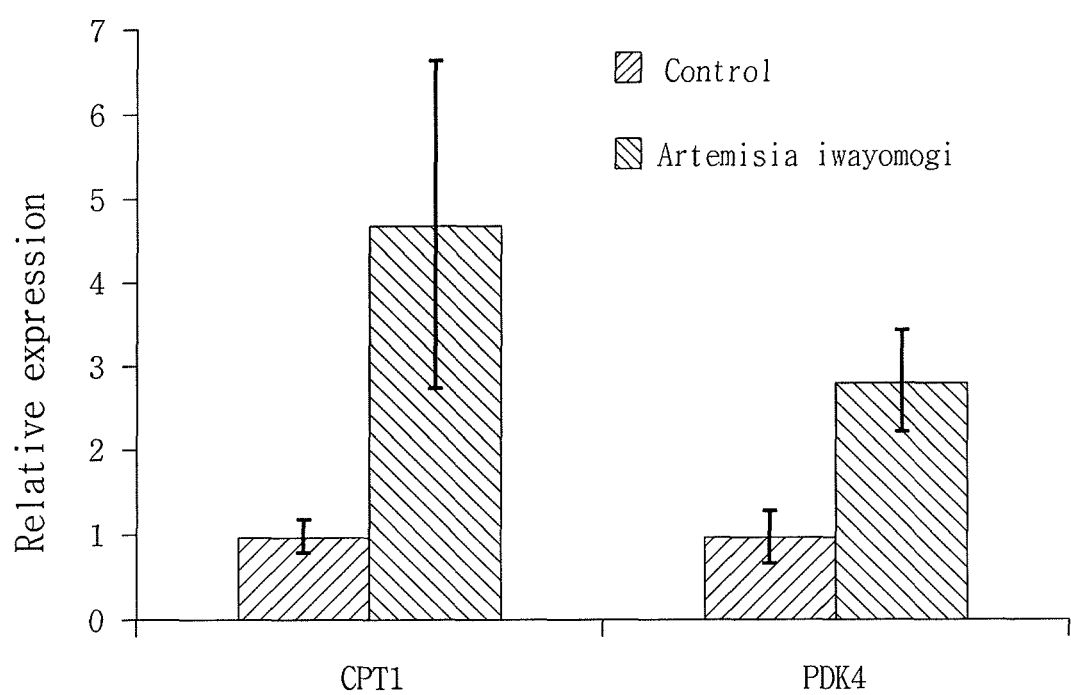
FIG. 3 shows expression level of the target genes of PPAR-δ, CPT1β and PDK4, in muscle cells treated with 200 µg/mL *Artemisia iwayomogi* extract.
Figure 4:
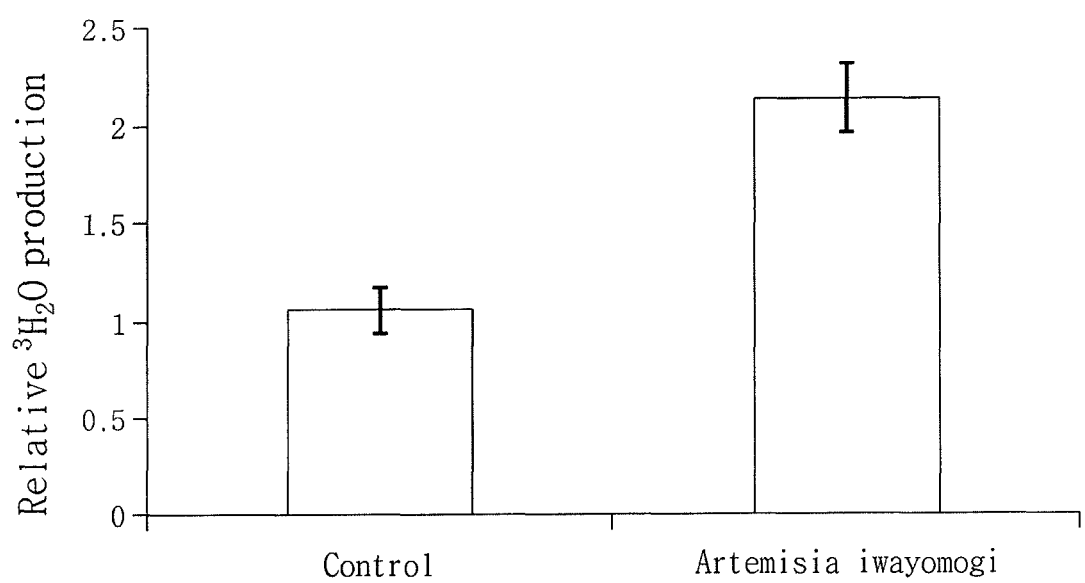
FIG. 4 shows fatty acid oxidation in muscle cells promoted as a result of treating with 200 µg/mL *Artemisia iwayomogi* extract.

The result is shown in FIG. 3. As seen from FIG. 3, it was confirmed that the *Artemisia iwayomogi* extract increases expression of CPT1β and PDK4 in the muscle cells when compared to control.

Test Example 4

Promotion of Fatty Acid Oxidation in Muscle Cells of *Artemisia iwayomogi* Extract C2C12 muscle cells differentiated for 4 days as in Test Example 3 were treated with the *Artemisia iwayomogi* extract for 24 hours. The next day, the cells were washed 2 times with brine after removing the medium. After treating with 1 mM L-carnitine and 3 μCi [9,10]-$^3$H palmitic acid for 3 hours, excess [9,10]-$^3$H palmitic acid was removed from the medium and the quantity of produced $^3H_2O$ was measured using a beta counter. As a result, it was confirmed that the cells treated with the *Artemisia iwayomogi* extract showed fatty acid oxidation increased by about 2 times as compared to the cells treated only with DMSO (control).

The invention claimed is:

1. A method for promoting activity of peroxisome proliferator-activated receptor delta (PPAR-δ) in skeleton muscle cells of a subject in need, comprising:
    administering an effective amount of *Artemisia iwayomogi* ethanol extract as an active ingredient,
    wherein the subject is in need of strengthening muscles or improving endurance.

2. The method for promoting activity of peroxisome proliterator-activated receptor delta (PPAR-δ) in skeleton muscle cells according to claim 1, wherein the *Artemisia iwayomogi* ethanol extract is administered in a form of a composition and the composition comprises the *Artemisia iwayomogi* ethanol extract in an amount of 1-80 wt % based on the total weight of the composition.

3. A method for promoting activity of peroxisome proliferator-activated receptor delta (PPAR-δ) in skeleton muscle cells of a subject in need, comprising:
    administering an effective amount of *Artemisia iwayomogi* ethanol extract as an active ingredient,
    wherein the subject is in need of strengthening muscles or improvinq endurance,
    wherein the active ingredient regulates expression of one or more genes that promote fat metabolism in at least skeletal muscle cells, thereby strengthening muscle cells or improving endurance in the subject.

* * * * *